United States Patent [19]

Templeton

[11] Patent Number: 4,934,152

[45] Date of Patent: Jun. 19, 1990

[54] APPARATUS AND METHOD FOR PRODUCING STERILE SLUSH AND HEATED STERILE LIQUID

[75] Inventor: Robert J. Templeton, Danville, Ind.

[73] Assignee: SaniServ Inc., Indianapolis, Ind.

[21] Appl. No.: 377,461

[22] Filed: Jul. 10, 1989

[51] Int. Cl.$^5$ .............................................. F25C 1/00
[52] U.S. Cl. ........................................... 62/66; 4/655;
                                             62/342; 128/846
[58] Field of Search ........................... 62/66, 340, 342;
        128/846, 849; 4/DIG. 18, 452, 484, 580, 655;
                                                      165/63

[56] References Cited

U.S. PATENT DOCUMENTS

| | | | |
|---|---|---|---|
| 1,860,302 | 5/1932 | Thomas | 165/63 |
| 1,987,020 | 1/1935 | Looft | 4/DIG. 18 |
| 2,817,851 | 12/1957 | Barnwell | 4/DIG. 18 |
| 3,024,471 | 3/1962 | Anderson | 4/DIG. 18 |
| 3,675,250 | 7/1972 | Bengtsson | 4/484 X |
| 4,393,659 | 7/1983 | Keyes et al. | 62/66 |

Primary Examiner—William E. Tapolcai
Attorney, Agent, or Firm—Woodard, Emhardt, Naughton Moriarty & McNett

[57] ABSTRACT

A surgical slush system for producing a sterile, semi-frozen slush from a sterile liquid. The system includes a slush generating unit having a cabinet with a plurality of louvres for air circulation, a basin at the top of the cabinet, a refrigeration means inside the cabinet for cooling the basin to a temperature below the freezing point of the sterile liquid, and a heating means for heating the basin to a temperature above the freezing point of the sterile liquid. A sterilized drape covers the basin. The drape is impervious to the sterile liquid and is sufficiently flexible to conform substantially to the interior shape of the basin with the sterile liquid being directly contained by the drape within the basin. An air filter in the form of a thin flexible sterilized sheet is fixed to and extends outwardly from the margin of the drape and is sized to extend over the louvres.

13 Claims, 2 Drawing Sheets

APPARATUS AND METHOD FOR PRODUCING STERILE SLUSH AND HEATED STERILE LIQUID

BACKGROUND OF THE INVENTION

The present invention relates generally to the field of medical devices and, more particularly, to devices for producing sterile ice and heated sterile liquid for surgical procedures and the like.

It is well known in the field of medicine to freeze a suitable sterile liquid such as saline for use in connection with surgical procedures. For example, in transplant surgery it is desirable to reduce the temperature of the body cavity after the organ has been removed to reduce bleeding. Thereafter, once the new organ has been transplanted, the sterile ice is replaced with a quantity of warm sterile saline solution to facilitate warming the body cavity back up to normal body temperature.

A relatively crude and laborious means which has been employed to produce the sterile ice is to simply freeze the sterile liquid in a bag and then break apart or crush the contents to render it suitable for use. Not only is it difficult to employ this procedure and result in a sterile ice product of uniform consistency, it is also possible to puncture or tear the bag and unintentionally spill the contents.

U.S. Pat. No. 4,393,659 to Taylor Keyes et al discloses a method and apparatus for producing sugical sterile ice having a semi-frozen or slush consistency. Unfortunately, the device and method disclosed therein has at least several disadvantages. For example, the device requires the use of a removable stainless steel product basin which must be continually reused and resterilized. Further, an alcohol or hospital grade glycol liquid is employed as a heat transfer medium between the heat transfer basin and the product basin. Such liquids may be are highly flammable or toxic, thereby creating possible fire hazards during use as well as further complicating the procedure. Yet further, although intended for use in a highly sterile environment, the interior of the machine can over time accumulate dust which during operation can be blown externally by air circulating through the louvres in the machine cabinet. In addition, the machine does not have any capability to heat the sterile liquid.

SUMMARY OF THE INVENTION

In accordance with one embodiment of the present invention there is provided a surgical slush system and method for producing a sterile, semi-frozen slush from a sterilized liquid. The system may be generally characterized as comprising a slush generating unit including a cabinet, a basin at the top of the cabinet, and a refrigeration means inside the cabinet for cooling the basin to a temperature below the freezing point of the sterilized liquid. The refrigeration means includes an evaporator mounted to the underside of the basin in heat transfer relationship therewith. The system may further be characterized as having a thin sterilized drape which is impervious to the sterile liquid and sized to cover the basin. The drape is sufficiently flexible to conform substantially to the interior shape of the basin and is removable therefrom. In use, the drape directly abuts the basin along substantially the entire surface of the basin. A sterilized liquid is directly contained by the drape within the basin.

As another aspect of the present invention there is provided a combination sterilized drape and air filter for use with a surgical slush machine of a type having a cabinet including a plurality of sides and a plurality of louvres along one or more of the sides thereof sized for passage of air therethrough to facilitate heat transfer inside the machine and a basin at the top of the cabinet. The combination sterilized drape and air filter comprises a sterilized drape including a thin sheet formed of a material which is impervious to the sterile liquid and sized to cover the basin while also being sufficiently flexible to conform substantially to the interior shape of the basin. There is also provided an air filter formed of a thin flexible sterilized sheet fixed to and extending outwardly from the margin of the drape and sized to extend over the louvres. The air filter sheet is pervious to air but substantially impervious to dust particles.

Accordingly, it is an object of the present invention to provide an improved method and system for producing a sterile, semi-frozen slush from a sterilized liquid and for heating sterilized liquid.

It is a further object of the present invention to provide a combination sterilized drape and air filter which directly contains the sterile liquid and prevents dust particles inside the surgical slush unit from contaminating the sterile environment externally thereof.

Related objects and advantages of the present invention will become more apparent by reference to the following figures and detailed description.

DESCRIPTION OF THE PREFERRED EMBODIMENT

Figure 1:
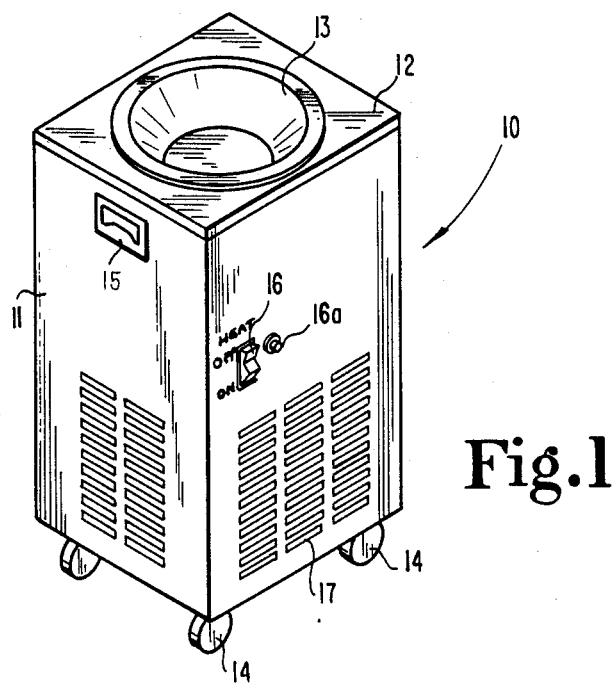
FIG. 1 is a perspective view of the slush generating unit of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
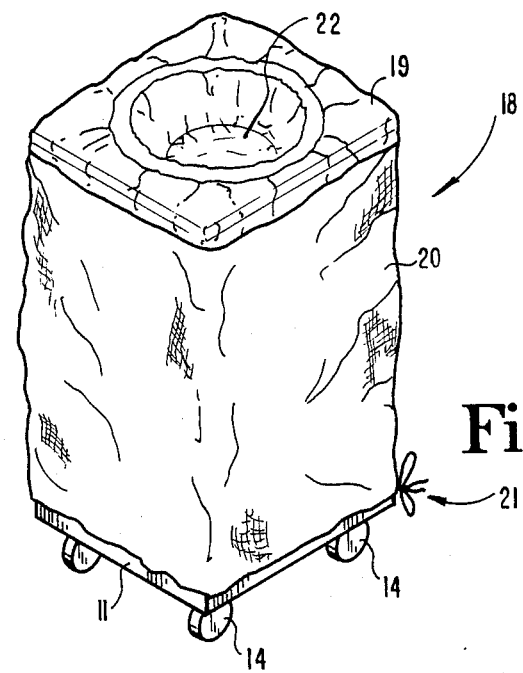
FIG. 2 is a perspective view of the slush generating unit of FIG. 1 with the combination sterilized drape and air filter mounted thereon.

Referring to the drawings in detail, FIG. 1 shows the slush generating unit of the present invention generally designated at 10. The slush generating unit 10 contains the cooling and heating systems for producing either sterile slush ice or heated sterile liquid for use during surgical procedures. Slush generating unit 10 includes an outer cabinet 11 of stainless steel construction, the top portion 12 of which is provided with a basin 13 of similar construction rigidly mounted therein. Basin 13 serves to contain the surgical sterile liquid, typically a saline solution, in a manner which will be fully described later herein. Wheels 14 and hand grips 15 on opposed sides of cabinet 11 facilitate easy transportation of unit 10, an especially convenient feature when dealing with cramped space conditions during surgery. As a further convenience, the height of top portion 12 is preferably sized to correspond to the height of a standard surgical instrument table. An externally mounted three-way switch 16 controls the operation of slush generating unit 10 and is manually activated among "COOL", "OFF" and "HEAT" positions. A red indicator light 16a lights when switch 16 is in the "HEAT" position to serve as a further visual indicator to distinguish that setting from the "COOL" and "OFF" settings, it being noted that the switch 16 is covered during operation by the combination drape/air filter as depicted in FIG. 2. A plurality of louvres 17 extend along one or more sides of cabinet 11 to provide intake and exhaust openings through which air is circulated inside cabinet 10 to facilitate heat transfer from cooling and heating systems residing internally thereof which will be described hereinafter.

Referring now also to FIG. 2, a combination drape/air filter 18 is shown covering the slush generating unit 10. The drape/air filter 18 has a unitary construction and includes a drape portion 19 coextensive with the top portion 12 and basin 13 of cabinet 11 and an air filter portion 20 sewed to the outer margin of drape portion 19 and which is formed to extend fully around the cabinet 11 and downwardly along the sides thereof a sufficient distance to fully cover the louvres 17. A drawstring 21 extends around air filter portion 20 along the lowermost portion and serves to seal the space between the cabinet 11 and air filter portion 20 below louvres 17.

The purpose of drape portion 19 is to directly contain a desired quantity of surgical sterile liquid 22 within basin 13 and maintain its sterility in use. Therefore, drape portion 19 must be formed of a material which is impervious to the sterile liquid 22. Further, drape portion 19 should be sufficiently flexible to conform to the interior shape of basin 13 with a minimum of air pockets therebetween so as to facilitate heat transfer between the surgical sterile liquid 22 and basin 13. In addition, the thickness of drape portion 19 should be minimized to enhance its heat transfer characteristics while being sufficiently thick to resist tearing or puncturing during normal use. Preferably, drape/air filter 18 is designed to be disposable after one time use and provided to the user presterilized and prepackaged in a leak proof bag or other suitable sealed container which preserves sterility during storage. While there are a range of conventionally known materials which meet these design constraints, Duraflex ™ PS8020F, clear polyruethane film manufactured by Deerfield Urethane, Inc. of South Deerfield, Mich. is presently preferred.

Air filter portion 20 serves as a sterile cover or barrier to prevent direct contact with the sides of unit 10 which is not capable of being sterilized to surgical sterile condition. It is to be noted that during operation of unit 10 air being exhausted through louvres 17 can contain contaminated dust particles which accumulate inside cabinet 11 during periods of nonuse. To address this problem, air filter portion 20 is formed of a material which is pervious to air but substantially impervious to such airborne particulate contaminants. Moreover, as with drape portion 19, air filter portion 20 is preferably made of a material suitable for one time disposable use. While there are a range of materials which are suitable for these purposes and which meet these design constraints, 0.8 oz. per square yard density span bonded polypropylene fabric manufactured by VWR Textiles and Supplies, Inc. of Hickory, N.C. is presently preferred.

Figure 3:
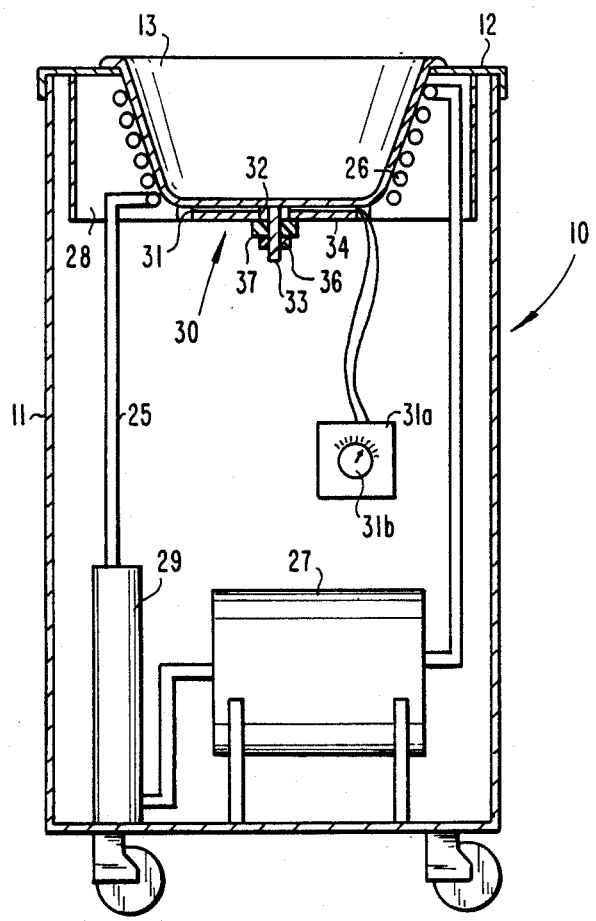
FIG. 3 is a section view schematically depicting interior components of the slush generating unit of FIG. 1.

Referring now also to FIG. 3, the construction of the refrigeration and heating means inside cabinet 11 will now be described. Refrigeration means 25 includes an evaporator 26 comprising a series of coils of conducting tubing suitably mounted, such as by soldering or brazing, in a close heat transfer relationship with basin 13 on the underside of basin 13 coextensive with the downwardly sloping sides thereof. A suitable insulation material 28, preferably polyurethane foam, is disposed around the exposed portions of the coils of conducting tubing and underside of basin 13. Evaporator 26 is connected in a closed refrigeration loop with compressor 27 and condenser 29. In the preferred embodiment, compressor and condensor are fan cooled by air circulated through louvres 17.

Heating means 30 includes an electrical heating element 31 disposed on the bottom underside of basin 13 and a thermostat 31a internally mounted inside cabinet 11 which selectively adjusts the heating level of element 31 by way of a manually rotatable selector dial 31b. The heating element 31 is in the shape of a thin wafer with a centrally located circular opening 32 through which threaded stud 33 projects. Heating element 31 is secured to the underside of basin 13 by a suitable pressure sensitive adhesive which not only serves as a means of attaching the element to basin 13 but also facilitates heat transfer by eliminating any voids or air gaps therebetween. In the preferred embodiment, heating element 31 is a model no. 060060B6 heating element manufactured by Heatron of Leavenworth, Kans. A plate 34 having a shape which corresponds to that of heating element 31 is mounted to stud 33 by nut 36 and Teflon ® lock washer 37 and serves both as a means for dissipating excess heat from heating element 31 within cabinet 11 and as an additional means for securing heating element 31 against basin 13. Lock washer 37 is made from a suitable insulating material such as Teflon which minimizes the heat transfer between heating element 31 and stud 33, thereby serving to prevent an undesirable hot spot at the bottom center of basin 13 which might otherwise cause melting of the drape portion 19 during use.

The method for producing a sterile, semi-frozen surgical slush from a sterilized liquid and for heating the sterilized liquid in accordance with the apparatus of the present invention disclosed above will now be described.

The surgical slush unit 10 is prepared for use by covering the unit 10 with the combination drape/air filter 18 so that the interior of basin 13 is covered with the drape portion 19 and the air filter portion 20 extends downwardly therefrom along the sides of cabinet 11 so as to fully cover the louvres 17. Drawstring 21 is drawn and tied so as to seal the flow of air through louvres 17 between air filter portion 21 and cabinet 11. The part of the drape portion 19 which overlies the basin 13 is pressed into and against the interior surface of the basin 13 so as to loosely conform the drape portion 19 to the shape of basin 13 and thereby minimize wrinkles and folds which reduce the effectiveness of heat transfer between the basin 13 and drape portion 19. Use of the Dureflex ™ polyurethane film as the material for drape portion 19 is prefered because of the material's ability to conform closely and adhere to the curved surface of the basin 13, which is preferably made of stainless steel. A suitable quantity of surgical sterile liquid, such as saline solution, is poured into the basin shaped cavity defined by that part of the drape portion 19 which overlies basin 13. The weight of the surgical sterile liquid naturally tends to press the drape portion 19 into contact with the surface of basin 13 so as to further facilitate heat transfer therebetween.

Once the liquid is poured into basin 13, the refrigeration means in unit 10 is activated to cool the liquid by moving switch 15 to the "COOL" setting. As the sterilized liquid congeals against the interior surface of the drape portion 19, a suitable spatula or paddle (not shown) is employed to stir the liquid and scrape the semi-frozen liquid from the sides of drape portion 19. Preferably, the paddle is made of a material which is sterilizable and sufficiently soft and resilient to resist tearing the drape portion 19 during use. For added convenience to the user, the paddle may be designed for disposal after use and provided in a pre-sterilized kit along with the combination drape/air filter 18. Scraping and stirring of the sterile liquid proceeds until a desired quantity of loose, semi-frozen slush ice is produced having the consistency desired for the intended use, such as for packing into a body cavity to reduce the temperature of the body cavity during a surgical procedure.

Once the surgical procedure is performed, it is desirable to facilitate raising the body cavity back to its normal temperature by contact with a sterile liquid having a temperture which is elevated slightly with respect to normal body temperature, for example approximately 105° F. For this purpose, an additional quantity of sterile liquid is poured into the drape portion 19 overlying basin 13 and the heating means in unit 10 is activated by moving switch 16 to the "HEAT" position so as to activate heating element 31.

After use, the combination drape/air filter 18 is removed from unit 10 and disposed.

It is to be noted that the operation above described is intended to be performed within the surgical sterile environment of an operating room. Within this environment, the combination drape/air filter 18 provides a sterile barrier protecting against direct contact with unit 10, which cannot itself be sterilized to surgical sterility standards. In addition, air flowing through louvres 17 is filtered by filter portion 20 to remove particulate contaminants therefrom which may have accumulated on the surfaces of internal components of unit 10. Moreover, since the unit 10 does not directly contain the sterile liquid there is no need to sterilize basin 13 for reuse.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical slush system for producing a sterile, semi-frozen slush from a sterile liquid, comprising:
   a slush generating unit including
   a cabinet,
   a basin at the top of said cabinet,
   refrigeration means inside said cabinet with said basin directly contacting said refrigeration means, said refrigeration means for cooling said basin to a temperature below the freezing point of said sterile liquid, said refrigeration means including an evaporator mounted to the underside of said basin in heat transfer relationship therewith, and heating means for heating said basin to a temperature above the freezing point of said sterile liquid, said heating means including an electrical heating element mounted to the underside of said basin in heat transfer relationship therewith; and
   a sterilized drape, said drape being impervious to the sterile liquid and sized to cover and directly contact said basin, said drape also being sufficiently flexible to conform substantially to the interior shape of said basin whereby said sterile liquid is directly contained by said drape within said basin.

2. The system of claim 1 wherein said drape covers at least the top portion of said cabinet.

3. The system of claim 2 wherein said cabinet includes a plurality of louvres along one or more of the sides thereof sized for passage of air therethrough to facilitate heat transfer inside said cabinet, and said drape includes a sterilized air filter cover extending outwardly from the margins of said drape so as to extend over said louvres, said cover being pervious to air but substantially impervious to dust particles thereby serving to filter air passing through said louvres.

4. A method for producing a sterile, semi-frozen surgical slush from a sterilized liquid, comprising the steps of:
   (1) providing a surgical slush unit having a rigid basin and refrigeration means directly contacting said basin for cooling said basin to a temperature below the freezing point of said sterilized liquid;
   (2) covering the interior of said basin with a sterilized drape by directly contacting said drape with said basin and conforming said drape substantially to the interior shape of said basin;
   (3) introducing a quantity of sterilized liquid directly into said drape;
   (4) cooling said sterilized liquid within said drape by activation of said refrigeration means in said sterile slush unit so as to cause said sterilized liquid to congeal against the interior surface of said drape; and
   (5) scraping the congealed sterilized liquid off the interior surface of said drape as said cooling step is performed, thereby producing a quantity of semi-frozen sterile slush of desired consistency.

5. The method of claim 4 wherein said sterile slush unit further includes a heating means for heating said basin, and said method comprises the further step of:
   (6) heating a quantity of said sterilized liquid contained directly within said drape to a desired temperature which is elevated with respect to normal body temperature by activation of said heating means in said sterile slush unit.

6. The method of claim 5 wherein said heating step is performed after said cooling and said scraping steps.

7. The method of claim 4 or 5 wherein said sterile slush unit includes a plurality of louvres for circulation of air through said unit and said method comprises the further steps of:
   (7) providing a sterilized air filter cover extending outwardly from the margins of said drape, said cover being pervious to air but substantially impervious to dust particles; and
   (8) covering said louvres with said cover thereby filtering air passing through said louvres when said sterile slush unit is activated.

8. A combination sterilized drape and air filter for use with a machine for producing a sterile semi-frozen surgical slush from a sterile liquid, said machine having a cabinet including a plurality of sides and a plurality of louvres along one or more of the sides thereof sized for passage of air therethrough to facilitate heat transfer inside said machine and a basin at the top of said cabinet, said combination sterilized drape and air filter comprising:

- a sterilized drape including a thin sheet formed of a material which is impervious to the sterile liquid and sized to cover said basin, said drape also being sufficiently flexible to conform substantially to the interior shape of said basin; and
- an air filter formed of a thin flexible sterilized sheet fixed to and extending outwardly from the margin of said drape and sized to extend over said louvres, said sheet being pervious to air but substantially impervious to dust particles.

9. The combination sterilized drape and air filter of claim 8 and further comprising:

a sealing means for sealing the space between said air filter and said cabinet.

10. The combination sterilized drape and air filter of claim 9 wherein said sealing means includes a drawstring mounted to the outer margin of said air filter.

11. A surgical slush system for producing a sterile, semi-frozen slush from a sterilized liquid, comprising:
   a quantity of sterilized liquid;
   a slush generating unit including
      a cabinet including a plurality of louvres along one or more of the sides thereof sized for passage of air therethrough to facilitate heat transfer inside said cabinet,
      a basin at the top of said cabinet, and refrigeration means inside said cabinet for cooling said basin to a temperature below the freezing point of said sterilized liquid, said refrigeration means including an evaporator mounted to the underside of said basin in heat transfer relationship therewith;
   a thin sterilized drape, said drape impervious to said sterile liquid and sized to cover said basin, said drape flexibly conforming substantially to the interior shape of said basin, said drape directly abutting said basin along substantially the entire surface of said basin and removable therefrom, said sterilized liquid being directly contained by said drape within said basin; and
   an air filter including a thin flexible sterilized sheet fixed to and extending outwardly from the margin of said drape and sized to extend over said louvres, said sheet being pervious to air but substantially impervious to dust particles.

12. The system of claim 11 wherein said slush generating unit further includes a heating means for heating said basin to a temperature above the freezing point of said sterile liquid, said heating means including an electrical heating element mounted to the underside of said basin in heat transfer relationship therewith.

13. A surgical slush system for producing a sterile, semi-frozen slush from a sterilized liquid, comprising:
   a quantity of sterilized liquid;
   a slush generating unit including
      a cabinet,
      a basin at the top of said cabinet,
      refrigeration means inside said cabinet for cooling said basin to a temperature below the freezing point of said sterilized liquid, said refrigeration means including an evaporator mounted to the underside of said basin in heat transfer relationship therewith, and a heating means for heating said basin to a temperature above the freezing point of said sterile liquid, said heating means including an electrical heating element mounted to the underside of said basin in heat transfer relationship therewith,
      a mounting stud rigidly fixed to and extending from the underside of said basin,
      a cover plate mounted to said mounting stud on the underside of said basin beneath said electrical heating element, said cover plate serving to dissipate excess heat from said heating element within said cabinet, and
      a Teflon ® lock washer extending between said mounting stud and said cover plate and serving to insulate the connection therebetween; and
   a thin sterilized drape, said drape being impervious to said sterile liquid and sized to cover said basin, said drape flexibly conforming substantially to the interior shape of said basin, said drape directly abutting said basin along substantially the entire surface of said basin and removable therefrom, said sterilized liquid being directly contained by said drape within said basin.

* * * * *